US00PP19936P2

(12) United States Plant Patent
Anatriello

(10) Patent No.: US PP19,936 P2
(45) Date of Patent: Apr. 21, 2009

(54) ***ALTERNANTHERA* PLANT NAMED 'BRAZILIAN RED'**

(50) Latin Name: *Alternanthera dentala*
Varietal Denomination: Brazil Red

(75) Inventor: Lucilene Anatriello, San Jose do Rio Preto (BR)

(73) Assignee: Athena Mudas Ltda, Sao Jose do Rio Preto (BR)

( * ) Notice: Subject to any disclaimer, the term of this patent is extended or adjusted under 35 U.S.C. 154(b) by 36 days.

(21) Appl. No.: 11/823,256

(22) Filed: Jun. 27, 2007

(51) Int. Cl.
*A01H 5/00* (2006.01)

(52) U.S. Cl. ..... Plt./373
(58) Field of Classification Search ..... Plt./373, Plt./263
See application file for complete search history.

(56) References Cited

U.S. PATENT DOCUMENTS

PP16,442 P2 * 4/2006 Saul ..... Plt./373

* cited by examiner

*Primary Examiner*—Wendy C. Haas

(57) ABSTRACT

A new and distinct *Alternanthera* plant cultivar is disclosed, characterized by an upright, freely branching growth habit, bright pink and dark purple two-toned foliage, small, narrow leaves and small, round white flowers that last 3 months or more during the fall.

1 Drawing Sheet

Latin name of the genus and species; *Alternanthera dentata.*

Variety denomination: 'Brazilian Red'.

BACKGROUND OF THE INVENTION

The new cultivar is a product of a whole plant natural mutation. 'Brazilian Red' was discovered as a single plant by Lucilene Anatriello in a greenhouse of *Alternanthera dentata* plants on Sep. 10, 2005 in São José do Rio Preto, Brazil. The breeder selected the natural mutation of *Alternanthera dentata* for the best color and shape of the plant.

Asexual reproduction of the new cultivar 'Brazilian Red' by vegetative cuttings was performed in São José do Rio Preto, Brazil and Oxnard, Calif., and has shown that the unique features of this cultivar are stable and reproduced true to type on successive generations.

SUMMARY OF THE INVENTION

The cultivar 'Brazilian Red' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Brazilian Red.' These characteristics in combination distinguish 'Brazilian Red' as a new and distinct *Alternanthera* cultivar:

1. Upright, freely branching and vigorous growth habit;
2. Bright pink and dark purple two-toned foliage;
3. Small, narrow leaves; and
4. Small, round white flowers that last 3 months or more during the fall.

Plants of the new cultivar 'Brazilian Red' are similar to plants of the parent variety, *Alternanthera dentata,* in most horticultural characteristics, however, plants of the new cultivar 'Brazilian Red' differ primarily from the parent in foliage coloration. 'Brazilian Red' was selected for its very brightly colored foliage of bright pink and purple coloration.

In comparison to the commercially available variety 'Grenadine' (U.S. Plant Pat. No. 16,442), 'Brazilian Red' is from the species *A. dentata,* not the species *A. ficoidea.* Also, the new cultivar 'Brazilian Red' is taller and has a wider plant spread. Additionally, 'Brazilian Red' has a shorter internode length. Further, the new cultivar 'Brazilian Red' has smaller leaves and a different leaf shape. Finally, 'Brazilian Red' has bright pink interveinal areas and dark purple veinal areas with pink venation, while the 'Grenadine' foliage has darker brown interveinal areas and pink veinal areas.

BRIEF DESCRIPTION OF THE PHOTOGRAPH

The accompanying photograph in the drawing illustrates in full color a typical plant of 'Brazilian Red' grown in a 2 gallon container. One cutting was used in the pot. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'Brazilian Red' plants grown in Oxnard, Calif. during the month of August. The growing temperature ranged from 12° C. to 15° C. at night to 12° C. to 20° C. during the day. Measurements and numerical values represent averages of typical plant types.

Botanical classification: *Alternanthera dentata* cultivar 'Brazilian Red.'

Commercial classification: Upright calico plant or ruby leaf.

PROPAGATION

Time to rooting: 4 to 10 days at 22° C.
Root description: Fine, fibrous.

PLANT

Growth habit: Upright herbaceous perennial.
Height: Approximately 65 cm.
Plant spread: Approximately 35 cm.
Growth rate: Fast.
Branching characteristics: Freely branching.
Number of lateral branches per plant: 7.
Length of lateral branches: Approximately 23 cm.
Diameter of lateral branches: Approximately 1.3 cm.
Number of leaves per lateral branch: Approximately 104.
Age of plant described: Approximately 120 days.

FOLIAGE

Leaf:
*Arrangement.*—Opposite.
*Average length.*—Approximately 5.4 cm.
*Average width.*—Approximately 1.7 cm.
*Shape of blade.*—Oblanceolate.
*Apex.*—Acuminate.
*Base.*—Attentuate.
*Attachment.*—Petiolate.
*Margin.*—Entire.
*Texture of top surface.*—Lightly pubescent.
*Texture of bottom surface.*—Lightly pubescent.
*Leaf internode length.*—Approximately 1.9 cm.
*Color.*—Young foliage upper side: Near Red-Purple 60A. Young foliage under side: Near Red-Purple 60B. Mature foliage upper side: Interveinal area: Near Red-Purple 59B. Veinal Area: Near Purple 79A. Mature foliage under side: Interveinal area: Near Red-Purple 59C. Veinal Area: Near Purple 79A.
*Venation.*—
*Type.*—Pinnate.
*Venation color upper side.*—Near Red-Purple 59B.
*Venation color under side.*—Near Red-Purple 59B.
Petiole:
*Average length.*—Approximately 1 cm.
*Color.*—Near Purple 79A.
*Diameter.*—Approximately 0.1 cm.

FLOWER

Flowering habit: Sporadic.
Flower type: Small axillary clusters.
Natural flowering season: Fall to early winter.
Number of flowers per lateral branch: Between 1 and 5.
Flower longevity on plant: 3 months.
Persistence: Persistent.
Changes as flower ages: The flowers start very white and soft and turn to a creamy yellow with a dry texture.
Bud:
*Bud shape.*—Spherical.
*Bud length.*—Approximately 0.04 cm.
*Bud diameter.*—Approximately 0.04 cm.
*Bud color.*—Near Yellow-White 158D.
Flower:
*Shape.*—Round.
*Facing direction.*—Upright.
*Type.*—Simple.
*Aspect.*—Concave.
*Diameter of entire flower.*—Approximately 1 cm.
*Length of flower.*—Approximately 0.6 cm.
Petals:
*Appearance.*—Matte.
*Texture.*—Smooth.
*Length of petal.*—Between 0.02 and 0.06 cm.
*Width of petal.*—Between 0.01 and 0.03 cm.
*Apex shape of petal.*—Acuminate.
*Petal margin.*—Entire.
Color:
*At first opening.*—Near Yellow-White 158D.
*Upper surface at maturity.*—Near White 155B.
*Upper surface at fading.*—Near Yellow-White 158C.
Fragrance: None.

SEPAL

Number: 5, fused at the base.
Sepal length: Approximately 0.05 cm.
Sepal width: Approximately 0.01 cm.
Apex shape: Acuminate.
Margin: Entire.
Color: Near Green-White 157D.
Peduncle:
*Length.*—Approximately 6 cm.
*Diameter.*—Approximately 0.05 cm.
*Angle to stem.*—Acute.
*Strength.*—Moderate.
*Color.*—Near Grey-Purple 185B.
*Habit.*—Upright.
*Texture.*—Pubescent.

REPRODUCTIVE ORGANS

*Number of pistils per flower.*—1.
*Stigma shape.*—Needle-shaped.
*Stigma color.*—Near Yellow-White 158C.
*Style color.*—Near Yellow-White 158D.
*Style length.*—Approximately 0.04 cm.
*Pollen color.*—No pollen detected.

OTHER CHARACTERISTICS

Disease resistance: Neither resistance nor susceptibility to diseases or pests has been observed in this variety.
Drought tolerance/cold tolerance: Flowering plants are hardy to low temperatures about −2° C. Non-flowering plants are hardy in the approximate range of −3° C. to −6° C. depending upon duration of cold and amount of moisture in the soil. With adequate water plants are hardy to a high temperature between 40 and 45° C.
Fruit/seed production: Not observed because commercially the plants are discarded or the flowers removed before seed set occurs.

What is claimed is:

1. A new and distinct cultivar of *Alternanthera* plant named 'Brazilian Red' as herein illustrated and described.

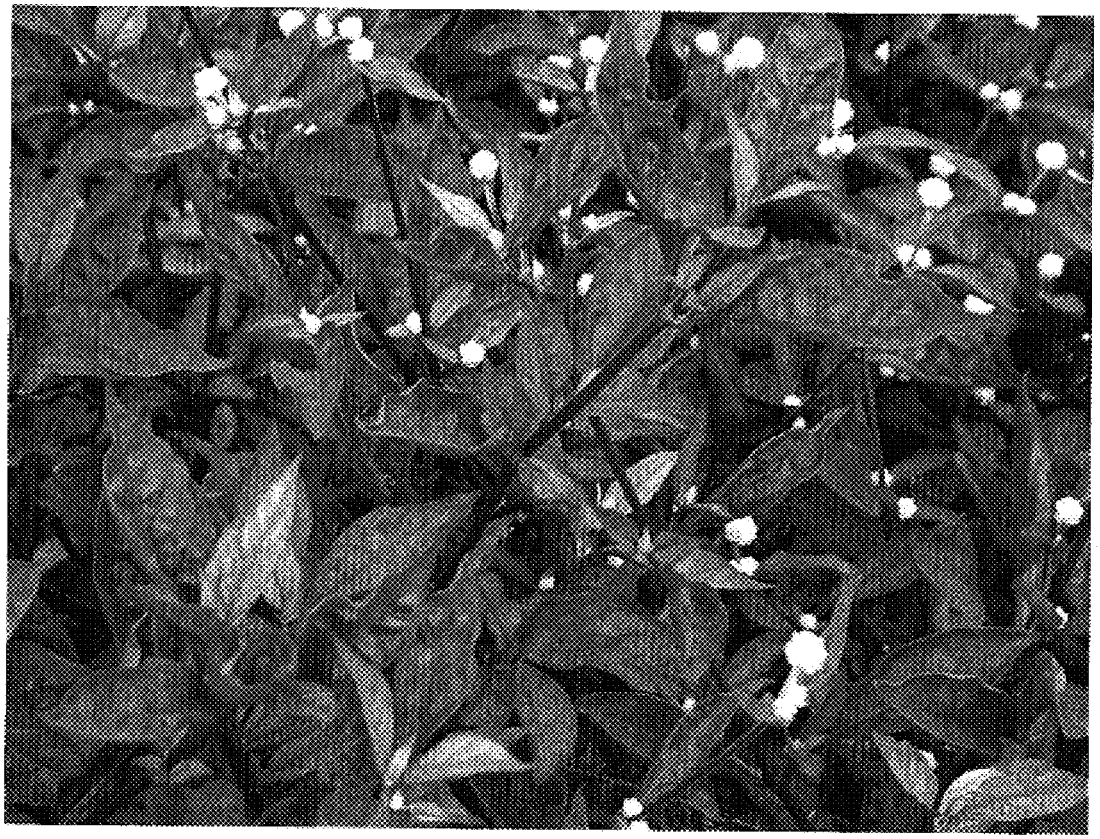

* * * * *